US006808557B2

(12) United States Patent
Holbrey et al.

(10) Patent No.: US 6,808,557 B2
(45) Date of Patent: Oct. 26, 2004

(54) CELLULOSE MATRIX ENCAPSULATION AND METHOD

(75) Inventors: John David Holbrey, Tuscaloosa, AL (US); Scott K. Spear, Bankston, AL (US); Megan B. Turner, Tuscaloosa, AL (US); Richard Patrick Swatloski, Tuscaloosa, AL (US); Robin Don Rogers, Tuscaloosa, AL (US)

(73) Assignees: The University of Alabama, Tuscaloosa, AL (US); PG Research Foundation, Darien, IL (US)

( * ) Notice: Subject to any disclaimer, the term of this patent is extended or adjusted under 35 U.S.C. 154(b) by 0 days.

(21) Appl. No.: 10/394,989

(22) Filed: Mar. 21, 2003

(65) Prior Publication Data

US 2004/0038031 A1 Feb. 26, 2004

Related U.S. Application Data

(63) Continuation-in-part of application No. 10/256,521, filed on Sep. 27, 2002.
(60) Provisional application No. 60/326,704, filed on Oct. 3, 2001.

(51) Int. Cl.[7] .......................... C08L 1/00; A01N 25/10; A61K 9/14; C05G 5/00; C12N 11/12

(52) U.S. Cl. ............................. 106/163.01; 106/200.2; 106/164.3; 106/501.1; 424/418; 424/493; 424/494; 71/23; 71/64.11; 71/64.13; 435/179; 426/650

(58) Field of Search .................... 106/163.01, 200.2, 106/164.3, 501.1; 424/418, 493, 494; 71/23, 64.11, 64.13; 435/179, 650

(56) References Cited

U.S. PATENT DOCUMENTS

| 1,943,176 A | | 1/1934 | Graenacher |
| 5,679,146 A | * | 10/1997 | Kalt et al. ............. 106/166.01 |
| 5,683,832 A | | 11/1997 | Bonhote et al. |
| 5,792,399 A | | 8/1998 | Meister et al. |
| 5,827,602 A | | 10/1998 | Koch et al. |

OTHER PUBLICATIONS

Bonhôte et al., "Hydrophobic, Highly Conductive Ambient–Temperature Molten Salts", Inorg. Chem. (1996) 35:1168–1178.
Fannin et al., "Properties of 1,3–Dialkylimidazollum Chloride–Aluminum Chloride Ionic Liquids. 2. Phase Transitions, Densities, Electrical Conductivities, and Viscosities", J. Phys. Chem. (1984) 88:2614–2621.
Fisher et al., "Structural Changes of Cellulose Dissolved in Molten Salt Hydrates", Book of Abstracts, 219th ACS national meeting, San Francisco, California (Mar. 26–30, 2000) (Abstract Only).

Gordon et al., "Fused Organic Salts. 8. Properties of Molten Straight–Chain Isomers of Tetra–n –pentylammonium Salts", J. Amer. Chem. Soc., (Nov. 22, 1978), 100(24):7445–7454.
Holbrey et al., "The Phase Behaviour of 1–Alkyl–3–Methlimidazolium Tetrafluoroborates; Ionic Liquids and Ionic Liquid Crystals", J. Chem. Soc., Dalton Trans. (1999) 2133–2139.
Huddleston et al., "Characterization and Comparison of Hydrophilic and Hydrophobic Room Temperature Ionic Liquids Incorporating the Imidazolium Cation", Green Chemistry (2001) no month provided 3:156–164.
Husemann et al., "Homogeneous Acetylation of Cellulose", Buletinul Institutului Politehnic din Iasi (1970) no month provided 16(1–2):47–51 (Abstract Only).
Leipner et al., "Structural Changes of Cellulose Dissolved in Molten Salt Hydrates", Macromol. Chem. Phys., (2000) no month provided 201(15):2041–2049.
Linko et al., "Cellulose Bead Entrapped Microbial Cells for Biotechnical Applications", Enzyme Microb. Technol. (1979) no month provided 1:26–30.
Maia et al., "Cellulose Organic Solvents. I The Structures of Anhydrous N–Methylmorpholine N–Oxide and N–Methylmorpholine N–Oxide Monohydrate", Acta. Cryst., (1981) no month provided 1:26–30.
Marson et al., "A Novel, Efficient Procedure for Acylation of Cellulose Under Homogeneous Solution Conditions", J. of Applied Polymer Science (1999) no month provided 74:1355–1360.
Ngo et al., "Thermal Properties of Imidazolium Ionic Liquids", Thermochimica Acta (2000) no month provided 357–358:97–102.
Shriver et al., Inorganic Chemistry, W.H. Freeman & Co. (New York:1990), no month provided pp. 406–407.
Suarez et al., "Synthesis and Physical–Chemical Properties of Ionic Liquids Based on 1–n –butyl–3–methylimidazolium Cation", J. Chim. Phys. (1998) no month provided 95:1626–1639.
Swatloski et al., "Dissolution of Cellose with Ionic Liquids", J. Am. Chem. Soc. (2002) no month provided 124:4974–4975.

(List continued on next page.)

Primary Examiner—David Brunsman
(74) Attorney, Agent, or Firm—Welsh & Katz, Ltd.

(57) ABSTRACT

A regenerated cellulose-encapsulated active substance and a method for encapsulating an active substance in a regenerated cellulose matrix are disclosed. The distribution of the active substance is preferably substantially homogeneous within the matrix of regenerated cellulose. The regenerated cellulose (i) has about the same molecular weight as the original cellulose from which it is prepared (ii) is substantially free of added substituent groups relative to the starting cellulose and is also substantially free of entrapped ionic liquid degradation products.

27 Claims, 7 Drawing Sheets

OTHER PUBLICATIONS

Weckstrom et al., in *Food Engineering in Food Processing*, vol. 2, Applied Science Publishers Ltd., pp. 148–151 (1979) no month provided.

Wilkes et al., "Air and Water Stable 1–Ethyl–3–methylimidazolium Based Ionic Liquids", *J. Chem. Soc., Chem Commun.* (1992) no month provided 965–967.

* cited by examiner

CELLULOSE MATRIX ENCAPSULATION AND METHOD

CROSS-REFERENCE TO RELATED APPLICATIONS

This is a continuation-in-part of application Ser. No. 10/256,521, filed on Sep. 27, 2002, that claimed priority from provisional application Ser. No. 60/326,704 that was filed on Oct. 3, 2001.

TECHNICAL FIELD

The invention provides new materials and a novel method for their preparation by incorporating molecular, nanoscale, and macroscopic materials within a cellulose matrix. The process involves encapsulation or immobilization of the active solid substance in a cellulose framework by regenerating cellulose dissolved in an ionic liquid solvent in a regenerating solution. The active substance can be initially present in the ionic liquid, or in the regenerating solvent, either as a solution, or as a dispersion. The invention is applicable to molecular encapsulation and to entrapping of larger particles including enzymes, nanoparticles and macroscopic components, and to the formation of bulk materials with a wide range of morphological forms.

BACKGROUND ART

The use of ionic liquids as replacements for conventional organic solvents in chemical, biochemical and separation processes has been demonstrated. Graenacher first suggested a process for the preparation of cellulose solutions by heating cellulose in a liquid N-alkylpyridinium or N-arylpyridinium chloride salt, U.S. Pat. No. 1,943,176, especially in the presence of a nitrogen-containing base such as pyridine. However, that finding seems to have been treated as a novelty of little practical value because the molten salt system was, at the time, somewhat esoteric. This original work was undertaken at a time when ionic liquids were essentially unknown and the application and value of ionic liquids as a class of solvents had not been realized.

Ionic liquids are now a well-established class of liquids containing solely ionized species, and having melting points largely below 150° C. or most preferably 100° C. In most cases, ionic liquids (IL) are organic salts containing one or more cations that are typically ammonium, imidazolium or pyridinium ions, although many other types are known. The range of ionic liquids that are applicable to the dissolution of cellulose are disclosed in U.S. patent application Ser. No. 10/256,521, filed on Sep. 27, 2002, entitled "Dissolution and Processing of Cellulose Using Ionic Liquids", that claimed priority from provisional application Serial No. 60/326,704 that was filed on Oct. 3, 2001, and in Swatloski et al., *J. Am. Chem. Soc.* 2002, 124:4974–4975.

Traditional cellulose dissolution processes, including the cuprammonium and xanthate processes, are often cumbersome or expensive and require the use of unusual solvents, typically with a high ionic strength and are used under relatively harsh conditions. [Kirk-Othmer "Encyclopedia of Chemical Technology", Fourth Edition 1993, volume 5, p. 476–563.] Such solvents include carbon disulfide, N-methylmorpholine-N-oxide (NMMNO), mixtures of N,N-dimethylacetamide and lithium chloride (DMAC/LiCl), dimethylimidazolone/LiCl, concentrated aqueous inorganic salt solutions [$ZnCl/H_2O$, $Ca(SCN)_2/H_2O$], concentrated mineral acids ($H_2SO_4/H_3PO_4$) or molten salt hydrates ($LiClO_4.3H_2O$, $NaSCN/KSCN/LiSCN/H_2O$).

These traditional cellulose dissolution processes break the cellulose polymer backbone resulting in regenerated products that contain an average of about 500 to about 600 glucose units per molecule rather than the native larger number of about 1500 or more glucose units per molecule. In addition, processes such as that used in rayon formation proceed via xanthate intermediates and tend to leave some residual derivatized (substituent groups bonded to) glucose residues as in xanthate group-containing cellulose.

For example, U.S. Pat. No. 5,792,399 teaches the use of N-methylmorpholine-N-oxide (NMMNO) solutions of cellulose to prepare regenerated cellulose that contained polyethyleneimine (PEI). That patent teaches that one should utilize a pre-treatment with the enzyme cellulase to lessen the molecular weight to the cellulose prior to dissolution. In addition, it is taught that NMMNO decomposes at the temperatures used for dissolution to provide N-methylmorpholine as a degradation product that could be steam distilled away from the cellulose solution. The presence of PEI is said to lessen the decomposition of the NMMNO.

Other traditional processes that can provide a solubilized cellulose do so by forming a substituent that is intended to remain bonded to the cellulose such as where cellulose esters like the acetate and butyrate esters are prepared, or where a carboxymethyl, methyl, ethyl, $C_2$–$C_3$ 2-hydroxyalkyl (hydroxyethyl or hydroxypropyl), or the like group is added to the cellulose polymer. Such derivative (substituent) formation also usually leads to a lessening of the degree of cellulose polymerization so that the resulting product contains fewer cellobiose units per molecule than the cellulose from which it was prepared.

Thus, Linko and co-worker reported dissolving relatively low molecular weight cellulose (DP=880) in a mixture of N-ethylpyridinium chloride (NEPC) and dimethylformamide, followed by cooling to 30° C., incorporation of various microbial cells into the solution and then regeneration of the cellulose into a solid form by admixture with water. [Linko et al., *Enzyme Microb. Technol.*, 1:26–30 (1979).] That research group also reported entrapment of yeast cells in a solution of 1 percent cellulose dissolved in a mixture of NEPC and dimethyl sulfoxide, as well as entrapment using 7.5 to 15 percent cellulose di- or triacetates dissolved in several organic solvents. [Weckstrom et al., in *Food Engineering in Food Processing*, Vol. 2, Applied Science Publishers Ltd., pages 148–151 (1979).]

Entrapped materials have a wide number of uses, from controlled release systems to structural modifiers and sensor or reactive materials. The entrapped materials can be formulated as membranes, coatings or capsules. Methods are known for forming encapsulated products including emulsion polymerization, interfacial polymerization, desolution, emulsification, gelation, spray-drying, vacuum coating, and adsorption onto porous particles. Common materials used include polymers, hydrocolloids, sugars, waxes, fats, metals and metal oxides.

The use of membranes, coatings, and capsules for the controlled release of liquid materials is well known in the art of both agricultural and non-agricultural chemicals, including the preparation of graphic arts materials, pharmaceuticals, food, and pesticide formulations. In agriculture, controlled-release techniques have improved the efficiency of herbicides, insecticides, fungicides, bactericides, and fertilizers. Non-agricultural uses include encapsulated dyes, inks, pharmaceuticals, flavoring agents, and fragrances.

The most common forms of controlled-release materials are coated droplets or microcapsules, coated solids, including both porous and non-porous particles, and coated aggregates of solid particles. In some instances, a water-soluble encapsulating film is desired, which releases the encapsulated material when the capsule is placed in contact with water. Other coatings are designed to release the entrapped material when the capsule is ruptured or degraded by external force. Still further coatings are porous in nature and release the entrapped material to the surrounding medium at a slow rate by diffusion through the pores.

Materials have been formulated as emulsifiable concentrates by dissolving the materials in an organic solvent mixed with a surface-active agent or as an oily agent. In solid form, the insecticides have been formulated as a wettable powder in which the insecticide is adsorbed onto finely powdered mineral matter or diatomaceous earth, as a dust or as granules.

However, these conventional formulations pose a variety of problems such as the pollution of the environment caused by the organic solvent used in the emulsions or by the dust resulting from the wettable powders. Furthermore, for these formulations to have long-term residual effectiveness, an amount much higher than that used in normal application is required, and this increased amount can affect the environment or cause problems of safety. Other conventional microcapsules that encapsulate active insecticidal components are obtained through an interfacial polymerization reaction and are not ideal in terms of the production process or as an effective stabilized insecticide.

There is therefore a strong demand for a formulation that maintains a high degree of efficacy over long periods. Given this background, research and development are now actively under way to develop a superior microencapsulated formulation that can effectively replace the emulsifiable concentrate, interfacially-polymerized or wettable powders, and is safer to use.

Enzyme entrapment on solid supports is a well-established technique for improving stability and separations aspects in enzymatic transformations. Entrapment of enzymes on solid supports can result in improved stability to pH and temperature and aid in separation of the enzyme from the reaction mixture, and also for formation of enzyme electrodes for sensor applications.

There are four principal methods available for immobilizing enzymes: adsorption, covalent binding, entrapment, and membrane confinement. A common method for immobilization is to use polysaccharide activation in which cellulose beads are reacted under alkali conditions with cyanogen bromide. The intermediate produced is then covalently coupled with soluble enzymes. Examples are lactase, penicillin acylase, and aminoacylase enzymes.

Entrapment of enzymes within gels or fibers is a convenient method for use in processes involving low molecular weight substrates and products. Entrapment is the method of choice for immobilization of microbial, animal and plant cells. Calcium alginate is widely used. Enzymes can be entrapped in cellulose acetate fibers by formulation of an emulsion of the enzyme plus cellulose acetate in dichloromethane, followed by extrusion of fibers.

Entrapped enzyme methods have wide applicability, but the entrapped enzymes can be technically difficult to prepare and involve moderate to high costs. Hence, new methods of preparing entrapped enzymes are desirable.

The disclosure hereinafter describes the preparation of encapsulated materials in a cellulose matrix by dispersion and regeneration of IL/cellulose solutions containing an active substance into a regenerating liquid in which the IL is soluble and that is a non-solvent for cellulose and the active agent. It will be clear to those skilled in the art that this invention is applicable to the formulation of beads and fibers in which active agents are entrapped.

BRIEF SUMMARY OF THE INVENTION

The present invention contemplates a cellulose-encapsulated active substance and an encapsulation method for active substances to form a regenerated cellulose matrix in which the active substance is distributed throughout the matrix. The distribution of the active substance is preferably substantially homogeneous within the matrix of regenerated cellulose. The regenerated cellulose (i) has about the same molecular weight as the original cellulose from which it is prepared and typically a degree of polymerization (DP) of about 1200, and (ii) is substantially free of substituent groups and entrapped ionic liquid degradation products. The material to be encapsulated (active substance) is dispersed, preferably homogeneously, or dissolved in a hydrophilic ionic liquid that is substantially free of water, an organic solvent or nitrogen-containing base containing solubilized cellulose, and the cellulose is subsequently reformed (regenerated) as a solid in which the active substance is dispersed in the cellulose matrix, preferably homogeneously.

This method has advantages for formation of composites containing many solid substances which are desirable to encapsulate in a cellulose matrix, particularly for the incorporation of active agents that are not soluble in water or other common solvents, for example nanoparticles or macroscopic materials.

Matrices formed by this process are capable of effecting a slow rate of release of the encapsulated materials by diffusion through the shell to the surrounding medium, swelling in a liquid medium such as water, by slow, controlled degradation of the cellulose matrix structure, or by slow dissolution of the active substance from within the matrix.

Materials suitable for encapsulation include chemical-biological agents such as herbicides, insecticides, fungicides, bactericides, animal, insect, and bird repellent, plant growth regulators, fertilizers, and flavor and odor compositions, catalysts, photoactive agents, indicators, dyes, and UV adsorbents.

The final morphological form of the encapsulated composite depends on the regeneration process and on the desired applications of the materials. For example, high surface area beads, cylinders or flocs can be manufactured for filtration or separation applications, whereas thin films can be prepared for membrane and sensor uses.

Entrapment of biomolecules on solid supports is a well-established technique for improving pH and temperature stability particularly for enzymes and whole cells. Entrapment of biomolecules within a cellulose support can result in new materials for sensing and detection application.

Macroscopic magnetite particles can be incorporated into cellulose to prepare magnetically modified materials. These materials have a number of applications in magnetic fluidized bed extraction processes for protein and metal extraction or detection.

BRIEF DESCRIPTION OF THE DRAWINGS

In the drawings forming a portion of this disclosure.

DETAILED DESCRIPTION OF THE INVENTION

The present invention provides an encapsulation method for a wide range of materials referred to herein as active substances that can be effectively carried out to provide active substance substantially homogeneously distributed through out the regenerated cellulose matrix. The method uses encapsulation by dispersion or dissolution in a hydrophilic ionic liquid containing solubilized cellulose, that is substantially free of water, an organic solvent or nitrogen-containing base, followed by subsequent reformation of the cellulose as a solid matrix in which the active substance is dispersed in the matrix. The resulting material contains the active substance dispersed substantially homogeneously throughout the regenerated cellulose matrix.

A method for the preparation of new materials incorporating molecular, nanoscale and macroscopic materials within a cellulose matrix is contemplated. A contemplated method contemplates encapsulation of the active substance by regenerating a polymer matrix from a hydrophilic ionic liquid (IL) solution containing the active solid substance into a regenerating solution in which both the cellulose and the active substance are insoluble or difficult to dissolve is described; i.e., substantially insoluble.

More specifically, the method contemplates the steps of providing a homogeneous composition that contains cellulose and an active substance dissolved or dispersed in a hydrophilic ionic liquid and in which the ionic liquid solution is substantially free of water, a non-ionic organic solvent or nitrogen-containing base containing solubilized cellulose. That composition is contacted with a liquid non-solvent diluent in which both the cellulose and active substance are substantially insoluble to form a liquid phase and a regenerated solid cellulose phase as a matrix encapsulating the active substance and thereby form composite material that comprises a cellulose-encapsulated active substance. Residual hydrophilic ionic liquid is preferably thereafter removed. Examples of active substances include the incorporation of water-insoluble metal extractants, water-insoluble dyes, biomolecules, and magnetite particles of about 5 microns in diameter (largest dimension if not approximately spherical) that can be dispersed in the IL solution, either physically to form a suspension or colloid, or by dissolving the components in the IL solvent, and then regenerating the composite material.

The distribution of the active substance is preferably substantially homogeneous within the matrix of regenerated cellulose. The regenerated solid cellulose (i) has about the same molecular weight as the original cellulose from which it is prepared and typically contains a degree of polymerization number (DP) of about 1200, or more. That regenerated cellulose (ii) is substantially free of an increased amount of substituent groups relative to the starting cellulose and entrapped ionic liquid degradation products.

A minor amount of cellulose hydrolysis can take place during a contemplated dissolution and regeneration. However, the weight average molecular weight of the cellulose after regeneration is about 90 percent that of the cellulose prior to dissolution and regeneration. This result is contrary to that of U.S. Pat. No. 5,792,399 where the starting cellulose is treated with a cellulase in the presence of NMMNO in order to effect dissolution.

The substituent groups of which the regenerated cellulose is substantially free are those that were not present in the cellulose that was dissolved in the IL. Thus, for example, the hydroxyl groups of a natural cellulose can be oxidized to form oxo (substituents with C=O bonds) functionality such as ketones, aldehydes, or carboxylic acids, and natural cellulose can contain amounts of such functionalities. The dissolution/regeneration process used herein does not cause the formation of more than a few percent more of those groups than were originally present. Where oxidized cellulose that contains a high level of oxo functionality is used as the starting material such as where Regenerated Oxidized Cellulose U.S.P. (ROC), the regenerated cellulose again contains about the same amount of functionality (e.g., about 18 to about 24 percent carboxyl groups for ROC) after dissolution and regeneration as was present prior to those steps being carried out.

Another group of substituents of which the regenerated cellulose is substantially free are those substituents such as xanthate groups, $C_{2-C3}$ 2-hydroxyalkyl (e.g., 2-hydroxyethyl and 2-hydroxypropyl) groups, and carboxyl groups such as acetyl and butyryl that are used in other processes to dissolve cellulose.

The hydrophilic ionic liquid solution used herein is substantially free of water, a water- or alcohol-miscible organic solvent or nitrogen-containing base and contains solubilized cellulose. Contemplated organic solvents of which the solution is free include solvents such as dimethyl sulfoxide, dimethyl formamide, acetamide, hexamethyl phosphoramide, water-soluble alcohols, ketones or aldehydes such as ethanol, methanol, 1- or 2-propanol, tert-butanol, acetone, methyl ethyl ketone, acetaldehyde, propionaldehyde, ethylene glycol, propylene glycol, the $C_1-C_4$ alkyl and alkoxy ethylene glycols and propylene glycols such as 2-methoxyethanol, 2-ethoxyethanol, 2-butoxyethanol, diethyleneglycol, and the like.

The cations of a hydrophilic ionic liquid are preferably cyclic and correspond in structure to a formula selected from the group consisting of wherein $R^1$ and $R^2$ are independently a $C_1-C_6$ alkyl group or a $C_1-C_6$ alkoxyalkyl group, and $R^3$, $R^4$, $R^5$, $R^6$, $R^7$, $R^8$ and $R^9$ ($R^3-R^9$), when present, are independently a hydrido, a $C_1-C_6$ alkyl, a $C_1-C_6$ alkoxyalkyl group, or a $C_1-C_6$ alkoxy group. More preferably, both $R^1$ and $R^2$ groups are $C_1-C_4$ alkyl, with one being methyl, and $R^3-R^9$, when present, are preferably hydrido. Exemplary $C_1-C_6$ alkyl groups and $C_1-C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1-C_6$ alkoxy groups contain the above $C_1-C_6$ alkyl group bonded to an oxygen atom that is also bonded to the cation ring. An alkoxyalkyl group contains an ether group bonded to an alkyl group, and here contains a total of up to six carbon atoms.

It is to be noted that there are two iosmeric 1,2,3-triazoles. It is preferred that all R groups not required for cation formation be hydrido.

The phrase "when present" is often used herein in regard to substituent R group because not all cations have all of the numbered groups. All of the contemplated cations contain at least four R groups, which may be hydrido, although $R^2$ need not be present in all cations.

The phrases "substantial absence" and "substantially free" are used synonymously to mean that less than about 5 weight percent water is present, for example. More preferably, less than about one percent water is present in the composition. The same meaning is intended regarding the presence of a nitrogen-containing base.

An anion for a contemplated ionic liquid cation is a halogen ion (fluoride, chloride, bromide, or iodide), perchlorate, a pseudohalogen ion such as thiocyanate and cyanate or $C_1-C_6$ carboxylate. Pseudohalides are monovalent and have properties similar to those of halides [Schriver et al., *Inorganic Chemistry*, W. H. Freeman & Co., New York (1990) 406–407]. Pseudohalides include the cyanide ($CN^{-1}$), thiocyanate ($SCN^{-1}$), cyanate ($OCN^{-1}$), fulminate ($CNO^{-1}$), and azide ($N_3^{-1}$) anions. Carboxylate anions that contain 1–6 carbon atoms ($C_1-C_6$ carboxylate) and are illustrated by formate, acetate, propionate, butyrate, hexanoate, maleate, fumarate, oxalate, lactate, pyruvate, and the like.

A contemplated ionic liquid used herein is hydrophilic and therefore differs from the hydrophobic ionic liquids described in Koch et al. U.S. Pat. No. 5,827,602 or those of Bonhôte et al. U.S. Pat. No. 5,683,832 that contain one or more fluorine atoms covalently bonded to a carbon atom as in a trifluoromethanesulfonate or trifluoroacetate anion.

The contemplated solvent can also comprise mixtures of two, or more, of the contemplated ionic liquids.

It is preferred that all R groups that are not required for cation formation; i.e., those other than $R^1$ and $R^2$ for compounds other than the imidazolium, pyrazolium and triazolium cations shown above, be hydrido. Thus, the cations shown above preferably have a structure that corresponds to a structure shown below, wherein $R^1$ and $R^2$ are as described before.

A cation that contains a single five-membered ring that is free of fusion to other ring structures is more preferred. A cellulose dissolution method is also contemplated using an ionic liquid comprised of those cations. That method comprises admixing cellulose with a hydrophilic ionic liquid comprised of those five-membered ring cations and anions in the substantial absence of water to form an admixture. The admixture is agitated until dissolution is attained. Exemplary cations are illustrated below wherein $R^1$, $R^2$, and $R^3$–$R^5$, when present, are as defined before.

Of the more preferred cations that contain a single five-membered ring free of fusion to other ring structures, an imidazolium cation that corresponds in structure to Formula A is particularly preferred, wherein $R^1$, $R^2$, and $R^3$–$R^5$, are as defined before.

A

An N,N-1,3-di-($C_1$–$C_6$ alkyl)-substituted-imidazolium ion is a more particularly preferred cation; i.e., an imidazolium cation wherein $R^3$–$R^5$ of Formula A are each hydrido, and $R^1$ and $R^2$ are independently each a $C_1$–$C_6$-alkyl group or a $C_1$–$C_6$ alkoxyalkyl group. A 1-($C_1$–$C_6$-alkyl)-3-(methyl)-imidazolium [$C_n$-mim, where n=1–6] cation is most preferred, and a halogen is a preferred anion. A most preferred cation is illustrated by a compound that corresponds in structure to Formula B, below, wherein $R^3$–$R^5$ of Formula A are each hydrido and $R^1$ is a $C_1$–$C_6$-alkyl group or a $C_1$–$C_6$ alkoxyalkyl group.

B

A contemplated ionic liquid is liquid at or below a temperature of about 150° C., and preferably below a temperature of about 100° C. and above a temperature of about −100° C. For example, N-alkylisoquinolinium and N-alkylquinolinium halide salts have melting points of less than about 150° C. The melting point of N-methylisoquinolinium chloride is 183° C., and N-ethylquinolinium iodide has a melting point of 158° C. More preferably, a contemplated ionic liquid is liquid (molten) at or below a temperature of about 120° C. and above a temperature of minus 44° C. (−44° C.). Most preferably, a contemplated ionic liquid is liquid (molten) at a temperature of about −10° to about 100° C.

Cellulose can be dissolved without derivitization in high concentration in ionic liquids by heating to about 100° C., by heating to about 80° C. in an ultrasonic bath, and most effectively by using microwave heating of the samples using a domestic microwave oven. Using a microwave heater, it is preferred to heat the admixture of hydrophilic ionic liquid and cellulose to a temperature of about 100° to about 150° C.

A contemplated ionic liquid has an extremely low vapor pressure and typically decomposes prior to boiling. Exemplary liquification temperatures [i.e., melting points (MP) and glass transition temperatures ($T_g$)] and decomposition temperatures for illustrative N,N-1,3-di-$C_1$–$C_6$-alkyl imidazolium ion-containing ionic liquids wherein one of $R^1$ and $R^2$ is methyl are shown in the table below.

| Ionic Liquid | Liquification Temperature (° C.) | Decomposition Temperature (° C.) | Citation* |
|---|---|---|---|
| [$C_2$mim] Cl | | 285 | a |
| [$C_3$mim] Cl | | 282 | a |
| [$C_4$mim] Cl | 41 | 254 | b |
| [$C_6$mim] Cl | −69 | 253 | |
| [$C_8$mim] Cl | −73 | 243 | |
| [$C_2$mim] I | | 303 | a |
| [$C_4$mim] I | −72 | 265 | b |
| [$C_4$mim] [$PF_6$] | 10 | 349 | b |
| [$C_2$mim] [$PF_6$] | 58–60 | 375 | c, a |
| [$C_3$mim] [$PF_6$] | 40 | 335 | a |
| [i$C_3$mim] [$PF_6$] | 102 | | a |
| [$C_6$mim] [$PF_6$] | −61 | 417 | d |
| [$C_4$mim] [$BF_4$] | −81 | 403, 360 | d, e |
| [$C_2$mim] [$BF_4$] | | 412 | a |
| [$C_2$mim] [$C_2H_3O_2$] | 45 | | c |
| [$C_2$mim] [$C_2F_3O_2$] | 14 | About 150 | f | a) Ngo et al., Thermochim. Acta, 2000, 357, 97.
b) Fanniri et al., J. Phys. Chem., 1984, 88, 2614.
c) Wilkes et al., Chem. Commun., 1992, 965.
d) Suarez et al., J. Chim. Phys., 1998, 95, 1626.
e) Holbrey et al., J. Chem. Soc., Dalton Trans., 1999, 2133.
f) Bonhote et al., Inorg. Chem., 1996, 35, 1168.

Illustrative 1-alkyl-3-methyl-imidazolium ionic liquids, [$C_n$-mim]X [n=4 and 6, X=$Cl^-$, $Br^-$, $SCN^-$, $(PF_6)^-$, $(BF_4)^-$] have been prepared. The dissolution of cellulose (fibrous cellulose, from Aldrich Chemical Co.) in those illustrative ionic liquids under ambient conditions and with heating to 100° C., with sonication and with microwave heating has been examined. Dissolution is enhanced by the use of microwave heating. Cellulose solutions can be prepared very quickly, which is energy efficient and provides associated economic benefits.

A solution comprised of cellulose in a molten hydrophilic ionic liquid solvent that is substantially free of water or a nitrogen-containing base is contemplated for preparing a cellulose matrix encapsulated material. As such, such a liquid or solution contains about one percent or less water or a nitrogen-containing base. Thus, when a solution is prepared, it is prepared by admixing the ionic liquid and cellulose in the absence of water or a nitrogen-containing base to form an admixture.

As above, the ionic liquid is comprised of cations and anions that are preferably those discussed above. A more preferred solution is comprised of cellulose dissolved in a hydrophilic liquid whose cations contain a single five-membered ring free of fusion to other ring structures, as discussed previously. A contemplated solution can be used as is to carry out further reactions on the cellulose such as acylation to form cellulose acetate or butyrate, or for regeneration.

Cellulose displays high solubility in the ionic liquids. Viscous, birefringent liquid crystalline solutions are obtained at high concentration, e.g., about 10 to about 25 weight percent.

A contemplated solution of cellulose in an ionic liquid can contain cellulose in an amount of about 5 to about 35 weight percent of the solution. More preferably, the cellulose is present at about 5 to about 25 weight percent of the solution. More preferably still, the cellulose is present at about 10 to about 25 weight percent of the solution.

The weight ratio of cellulose to active substance in the molten composition can be quite varied. For example, a range of about 1000:1 to about 1:2 by weight of cellulose to active substance is contemplated. More usual weight ratios contemplated are about 100:1 to about 1:1. Those weight ratios are reflected also in the regenerated cellulose product.

Ionic liquids containing chloride anions appear to be most effective. The chloride anion is not required; reasonable solubility was also observed when the ionic liquid contained thiocyanate, perchlorate, and bromide anions. No solubility was observed for ionic liquids containing tetrafluoroborate or hexafluorophosphate anions.

In usual practice, cellulose is dissolved in an IL, to form a homogeneous, or liquid crystalline anisotropic solution. The material for incorporation is then introduced into the IL solution, either dissolved, or dispersed in the medium (for example nanoparticles or macroscopic beads). The cellulose matrix is then formed by regeneration upon contacting the IL solution with a non-solvent diluent, resulting in formation of a regenerated cellulose material (as a floc, film, membrane, fiber, or monolith depending on processing) in which the additives are entrained.

The order of addition of the components to the IL solvent is not important for the regeneration and encapsulation process, and depends on external consideration such as the stability of the individual components under processing conditions. Cellulose can be initially dissolved to form a solution in the IL, followed by dispersion of the active components, and regeneration. Or, the active component can be dispersed in the IL, followed by dissolution of cellulose and subsequent regeneration of the composite.

The regenerating fluid or non-solvent diluent is a non-solvent for the active substance and the cellulose. That is, the regenerating fluid does not dissolve large quantities of either the cellulose or the active agent, so that both ingredients are substantially insoluble in the regenerating fluid. Thus, the active substance and the cellulose are independently soluble to an extent of less than about 5 percent by weight, and preferably less than about 1 percent in the regenerating fluid. The ionic liquid is miscible with the regeneration fluid, and contacting of the IL phase with the regeneration fluid induces regeneration of the solid cellulose polymer that is the matrix in which the active substance is encapsulated.

Where extrusion of an ionic liquid solution of cellulose and an additive through a die is contemplated, that extrusion can be accomplished in a number of manners that are well known. For example, in some embodiments, a surface of the die containing one or more orifices through which the solution is extruded is below the surface of the regenerating fluid. In other embodiments, the solution passes from a die orifice through air or another gas such as nitrogen or argon prior to being contacted with the regenerating fluid.

The liquid non-solvent is preferably miscible with water. Exemplary liquid non-solvents include water, an alcohol such as methanol, or ethanol, acetonitrile, an ether such as furan or dioxane, and a ketone such as acetone. The advantage of water is that the process avoids the use of a volatile organic compound (VOC). Regeneration does not require the use of volatile organic solvents. The ionic liquid can be dried or otherwise freed of the liquid non-solvent and reused after regeneration.

This method has advantages for formation of composites containing many solid substances that it can be desirable to encapsulate in a cellulose matrix, but that are not soluble in an ionic liquid, for example nanoparticles or macroscopic materials.

The concept described herein permits addition of IL-soluble chemicals to be added, followed by regeneration using a non-solvent diluent in which both cellulose and additive are non- or sparingly soluble. Incorporation of nanoparticles, and macroscopic particles in the cellulose matrix that are initially dispersed within the viscous IL medium, results in a substantially homogeneous dispersion within the regenerated cellulose matrix, forming a nano-dispersed composite.

Engineered cellulose forms containing impregnated additives with enhanced properties and applications can be prepared from ionic liquid solution. Useful applications include, but are not limited to membranes/filters, fuel cells, separations devices, electrolysis membranes, flame retardants, biocidal filters, sensors, metal extractants, supports for enzymes, extractant materials for filtration, separations and extractions: metal ions, biomolecules, gas molecules, magnetic particles for membrane/extractant processing, materials modifiers for cellulose coatings, bioactive agents (controlled release, sensing, destruction), metal complexants (sensing, controlled release, extractants and binding and separations agents for filters), water insoluble dyes for coloring cellulose, sensing and indicators, photoresists, incorporation of nanoparticles as photonic agents or UV screens, magnetic particles for magneto-responsive beads, filtration and reactive beds, nanoparticle catalysis, dispersions of clays and other fire-retardant materials, enzyme supports, supported polymer electrolytes, cavity-forming pillars/scaffolding for the manufacture of nanoporous materials.

EXAMPLE A

Preparation of 1-Butyl-3-methylimidazolium Chloride [$C_4$mim]Cl

1-Butyl-3-methylimidazolium chloride [$C_4$mim]Cl was prepared using literature procedures [Huddleston et al., Green Chem., 2001, 3:156] from 1-chlorobutane and 1-methylimidazole (both from Aldrich Chemical Co., Milwaukee, Wis.), and was isolated as a colorless, anhydrous crystalline solid at room temperature.

All the initial IL solutions of cellulose were prepared following the methods disclosed in U.S. application Ser. No. 10/256,521 or application Ser. No. 60/326,704, both of which were referred to previously. Solutions prepared by microwave pulsing are typically about 110° to about 130° C. Active substances were typically added to the solution of cellulose in IL at a solution temperature of about 80 to about 90° C.

EXAMPLE 1

Incorporation of a Hydrophobic Metal Extractant into a Cellulose Matrix

The actinide complexant (complexing agent), carbamoyl methyl phosphine oxide, or CMPO (Strem Chemicals, Newburyport, Mass.) was incorporated into a reconstituted cellulose matrix to provide a solid supported metal extractant.

CMPO was encapsulated in a cellulose matrix (referred to as CMPO-cellulose). CMPO (20 weight percent with respect to cellulose) was added to a 10 weight percent solution of cellulose (microcrystalline, Aldrich) in [$C_4$mim]Cl ionic liquid solution at about 90 C, prepared via microwave heating. After vigorous stirring to ensure a homogenous distribution of CMPO throughout the cellulose-in-ionic liquid solution, CMPO-cellulose was reconstituted by transferring (via pouring) into a 1 L beaker containing 800 mL of deionized water. The contents of the beaker where rapidly stirred, and the water was refreshed 3 times to ensure compete removal of the ionic liquid. The resultant material resembles a floc, and was isolated via suction filtration.

Standards of microcrystalline cellulose prepared and reconstituted from the ionic liquid solution using the same procedure in the absence of CMPO, and untreated microcrystalline/cellulose used as received, were used as blanks for uptake measurements.

The presence of extractant in the reconstituted cellulosic matrix was confirmed by the observation of enhanced distribution of actinide ($^{241}$AmCl$_3$ in 1 M HCl, $^{239}$PuCl$_4$ in 1 M HNO$_3$, $^{233}$UO$_2$Cl$_2$ in dilute HNO$_3$) radiotracers to the CMPO-cellulose material from aqueous acid solution with respect to distributions for both untreated and reconstituted cellulose blanks. Measurements were made in 0.001 M, 0.01 M, 0.1 M, 1.0 M, and 10.0 M nitric acid solutions. All aqueous solutions were prepared in deionized water that was purified with a Barnstead deionization system (Dubuque, Iowa) and polished to 18.3 MΩ cm$^{-1}$.

The dry weight conversion factors for the cellulose, reconstituted cellulose, and CMPO-cellulose materials were determined as follows. A known mass of material was stirred in an excess of water for 24 hours at room temperature. This was followed by 10 min of conditioning (air drying) on a Buchner funnel. Once conditioned, samples were transferred to a preweighed crucible and dried in an oven at 110° C. until a constant mass was achieved. Each gravimetric analysis was preformed in triplicate. All materials were stored in tightly capped vials and were not exposed to air for any extensive period of time in order to maintain water content.

All weight distribution ratios were determined radiometrically via batch contacts of the cellulose, regenerated cellulose, and CMPO-cellulose materials with the desired solutions. The dry weight distribution ratio is defined as:

$$D_w = [(A_o - A_f)/A_f] * [V/(m_R * dwcf)]$$

where $A_o$ is the activity of the solution prior to contact, $A_f$ is the activity of the solution after contact, V is the volume (mL) of solution the material is contacted with, $m_R$ is the mass (g) of the cellulose or CMPO-cellulose material, and dwcf is the dry weight conversion factor that relates the mass of the hydrated material to its dry mass.

The $D_w$ studies were carried out as follows. The radiotracer was added to 1.3 mL of the solution of interest. This was vortexed for one min, and two 100 µL aliquots removed for radiometric counting ($A_o$) One mL of the remaining solution (V) was then added to a known mass of dry cellulose, hydrated regenerated cellulose, or hydrated CMPO-cellulose material ($m_R$) and centrifuged for one minute. The solution was then allowed to stir (ensuring that the cellulose materials are not just suspended in solution) for approximately 60 minutes. The contact time is believed to be sufficient for the systems to reach equilibrium. After completion of stirring, the samples were centrifuged for 2 minutes in order to completely separate the cellulose materials from the aqueous phase. A 100 µL aliquot ($A_f$) was then removed for counting. Counting for $^{239}$Pu and $^{233}$UO$_2$ were carried out using standard liquid scintillation analysis. Counting for $^{241}$Am was carried using standard γ (gamma) radiometric analysis. Duplicate radiometrically determined distributions ratios were consistent to ±5%.

Figure 1:
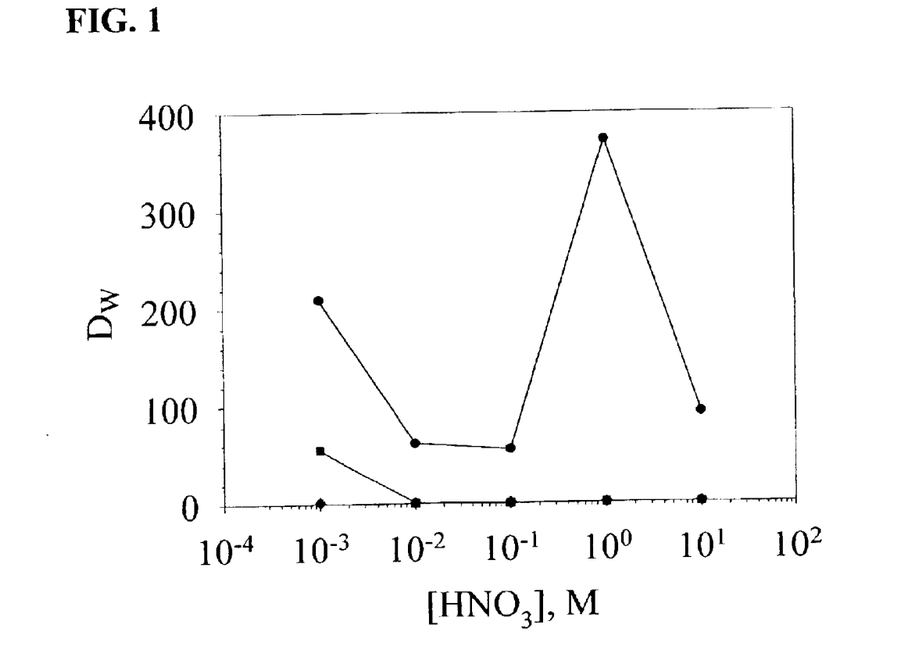
FIG. 1 is a graph of $D_w$ values for $^{241}$Am to CMPO impregnated cellulose (circles), cellulose only (squares) and regenerated cellulose (diamonds) from aqueous nitric acid solutions as a function of acid concentration.
Figure 2:
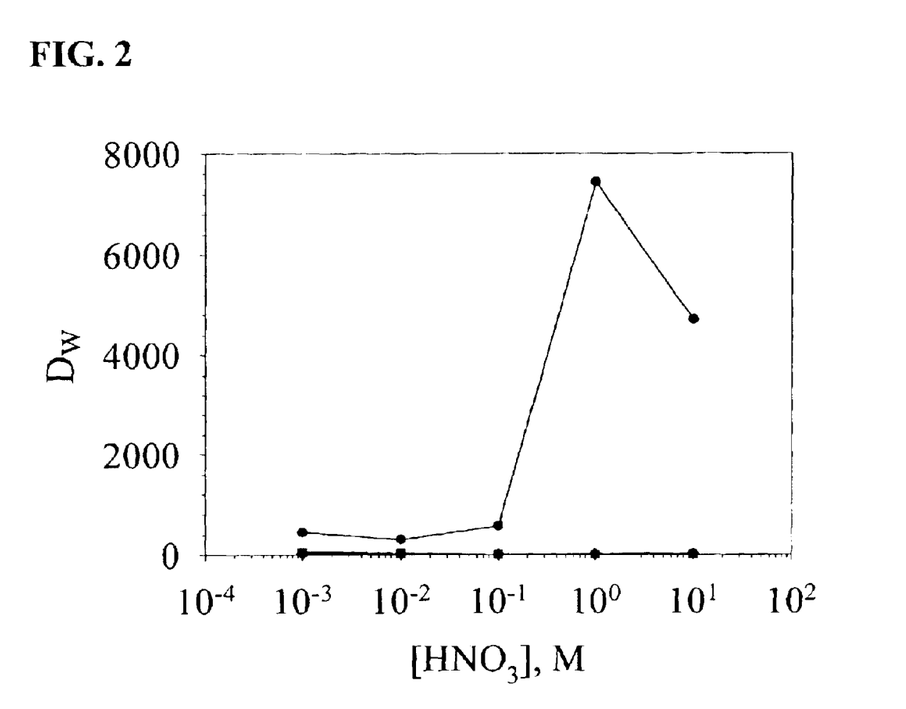
FIG. 2 is a graph of D values for $^{239}$Pu to CMPO impregnated cellulose (circles), cellulose only (squares) and regenerated cellulose (diamonds) from aqueous nitric acid solutions as a function of acid concentration.
Figure 3:
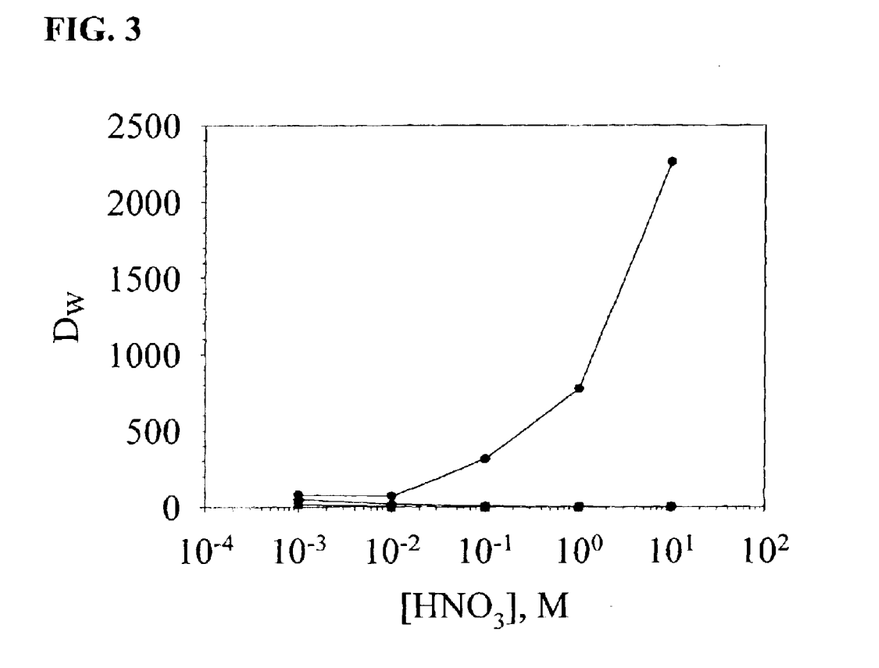
FIG. 3 is a graph of $D_w$ values for $^{233}$UO$_2$ to CMPO impregnated cellulose (circles), cellulose only (squares) and regenerated cellulose (diamonds) from aqueous nitric acid solutions as a function of acid concentration.

The results of these extraction studies are shown in FIGS. 1, 2 and 3. CMPO-cellulose successfully extracted the actinide from the nitric acid solution over a wide range of pH values, and the extractions were superior to those obtained using cellulose alone.

EXAMPLE 2

Incorporation of Protoporphyrin IX as a Further Hydrophobic Metal Extractant

Protoporphyrin IX (10 mg, CAS 553-12-8; Aldrich Chemical Co.), was added as a powder to a solution of cellulose (Whatman filter paper, 1 g) in molten [$C_4$mim]Cl (10 g), [prepared by microwave heating of cellulose in the IL with short pulses until a viscous, homogeneous solution was formed] and stirred until dissolved, resulting in a dark red-orange viscous solution containing cellulose (10 weight percent) and dye (0.1 weight percent). The cellulose was regenerated as a film by coating a glass sheet with a thin layer of the ionic liquid solution, followed by immersion into a bath containing deionized water. After immersion for 30 minutes, the orange cellulose film was removed from the regeneration bath and dried in air for 15 minutes to give a soft, pliable film. The wash water was uncolored indicating that none of the protoporphyrin IX had leached from the film.

The UV/vis spectrum of the film (transmission) showed the presence of the characteristic broad absorption band with a maximum at 400 nm from the Protoporphyrin IX metal extractant, enclosed within the film.

EXAMPLE 3

Formation of Colored Cellulose Products by Trapping of Dye Molecules

The non-reactive dye, Victoria blue B (50 mg, CAS 2185-86-6; J. T. Baker Chemical Company, NJ), was added as a powder at about 80° C. to a preformed solution of cellulose (Whatman filter paper, 1.5 g) in molten [$C_4$mim]Cl (30 g) [prepared by heating a slurry of the filter paper and [$C_4$mim]Cl at 120° C. for 5 hours with occasional stirring]. The resulting composition was stirred until the dye dissolved, resulting in an intense blue viscous solution containing cellulose (5 weight percent) and dye (0.15 weight percent). The cellulose was regenerated as a film by coating a glass sheet with a thin layer of the ionic liquid solution, followed by immersion into a bath containing deionized water. After immersion for 1 hour, the blue cellulose film was removed from the regeneration bath and dried in air for 15 minutes to give a soft, pliable film. The water was pale blue indicating that a small concentration of dye had leached from the film.

The UV/vis spectrum of the film (transmission) showed the presence of the characteristic broad absorption band with a maximum at 597 nm from the Victoria Blue B dye, enclosed within the film.

EXAMPLE 4

Formation of a pH-Sensitive Cellulose Film

Cellulose azure (10 mg, CAS 76296-24-7; Sigma Chemical Co., St. Louis, Mo.), a pH-sensitive dye molecule (Remazol Brilliant Violet 5R) covalently attached to a cellulose backbone, was added as a powder to a solution of cellulose (microcrystalline cellulose [9004-34-6], 1 g; Sigma) in molten [$C_4$mim]Cl (10 g). The initial cellulose in IL solution was formed by pulsed microwave heating of cellulose powder in [$C_4$mim]Cl, followed by cooling to about 90° C., at about which temperature the addition took place. The resulting composition was stirred until the blue powder dissolved, resulting in an intense blue viscous solution containing cellulose (10 weight percent) and cellulose azure (0.1 weight percent).

The cellulose was regenerated as a film by coating a glass sheet with a thin layer of the ionic liquid solution, followed by immersion into a bath containing deionized water. After immersion for 20 minutes, the blue cellulose film was removed from the regeneration bath and dried in air for 15 minutes to give a soft, pliable film. The wash water was uncolored indicating that none of the cellulose azure had leached from the film.

The sensitivity of the thus prepared cellulose-cellulose azure film to pH was tested by first immersing the membrane in a pH 7 buffer solution yielding a blue film. The film was then transferred to a solution of pH 2 buffer causing a color change in the film from blue to pink. This process was repeated with equivalent results several times and over the course of many months indicating that stability of the cellulose-cellulose azure pH sensitive film is long lasting.

Figure 4:
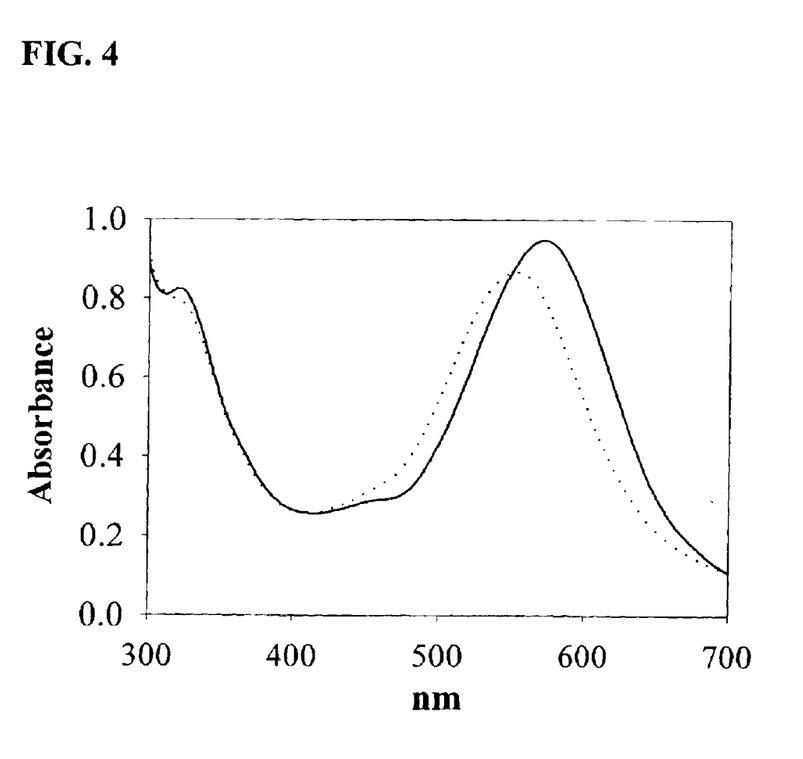
FIG. 4 is a UV/vis spectrum of a cellulose-cellulose azure film at pH 6.88 (solid line) and pH 2.10 (dotted line)

The UV/vis spectrum of the film (transmission) in FIG. 4 shows the pH sensitive cellulose-cellulose azure film with a blue absorption band with a maximum at 570 nm at pH 6.88 and a pink absorption band with a maximum at 550 nm at pH 2.10.

EXAMPLE 5

Encapsulation of Bovine Serum Albumin in a Cellulose Film

Bovine serum albumin (BSA) was added to a solution of cellulose (fibrous, Aldrich; 5 weight percent) dissolved in [$C_4$mim]Cl that was prepared by pulse microwave heating of the cellulose fibers in the IL until a viscous, homogeneous solution was obtained. The mixture was vortexed to disperse the BSA. A thin film was prepared by coating a microscope slide with the IL solution. Immersing the slide in a bath of deionized water regenerated the cellulose.

Figure 5:
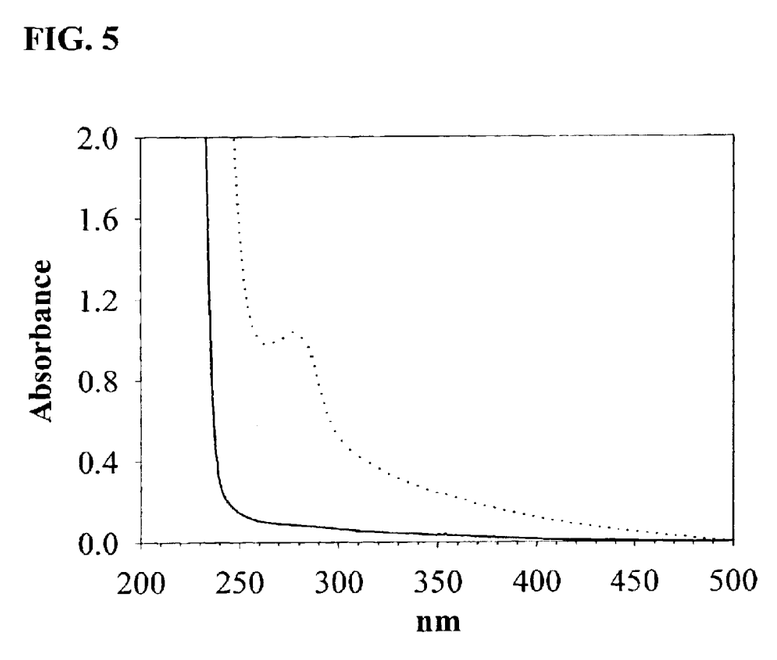
FIG. 5 is a UV/vis spectrum of a cellulose film alone (solid line) and a cellulose film containing bovine serum albumin (BSA; dotted line)

UV/Visible spectra of a regenerated cellulose matrix from an ionic liquid solution, and a regenerated cellulose matrix from an ionic liquid solution containing the protein, bovine serum albumin (BSA) were taken. The presence of an UV absorption peak centered at 280 nm in FIG. 5 is indicative of BSA entrapped within the cellulose film. This peak is characteristic to the solution phase UV spectra for BSA ($\lambda_{max}$=284 nm).

EXAMPLE 6

Encapsulation of Laccase and a Hydrophobic Ionic Liquid in Cellulose

Cellulose pulping sample (0.10 g), obtained from International Paper (degree of polymerization ~1,000), was introduced to 5.0 g [bmim]Cl and microwave-heated in 3–5 second pulses. Complete dissolution of the sample was achieved resulting in a viscous solution. Cellulosic matrix was cooled to room temperature to avoid heat-induced denaturation of the enzyme.

Figure 6:
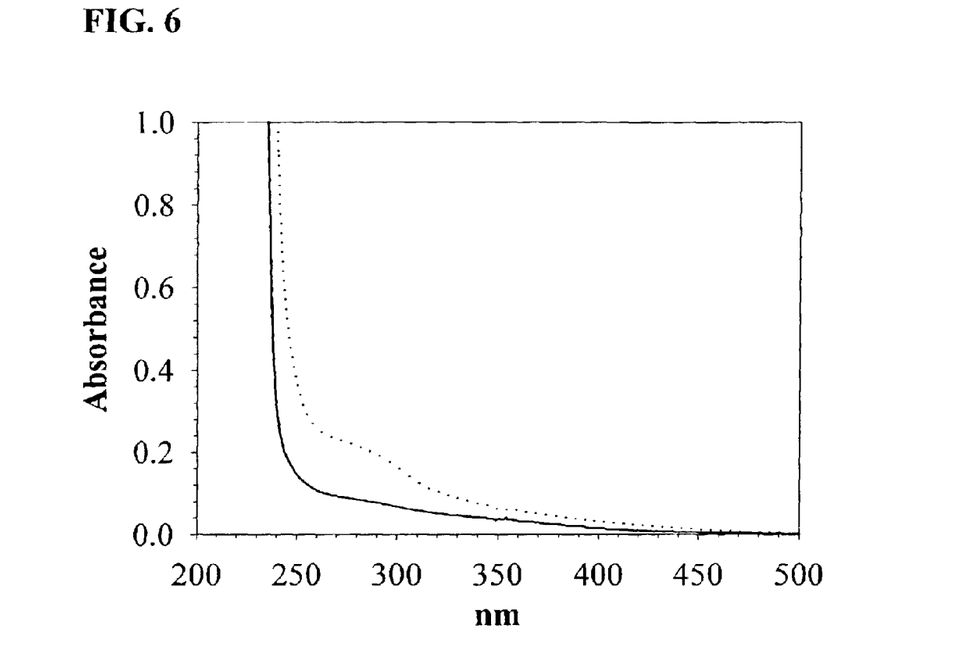
FIG. 6 is a UV/vis spectrum of a cellulose film alone (solid line) and cellulose film containing laccase (dotted line)

In a separate vial, 5.0 mg laccase was introduced into 5.0 g [bmim][$Tf_2$N] to serve as a 'protective' coating for the enzyme. The coated laccase was then added to the cooled IL/cellulose solution and immediately cast into a film. The film was washed with purified water three times to regenerate the cellulose and rid the film of excess ionic liquid. A portion of the film was added to 5.6 mL of a 50 mM phosphate buffer solution spiked with 200 uL syringealdizine solution [8.2 mg syringealdizine dissolved in 20 mL MeOH]. A UV/vis spectrum of the film indicated incorporation of the enzyme into the regenerated cellulose matrix by the maximum absorption at about 280 nm, as is shown in FIG. 6. The colorless film was left in solution overnight (about eighteen hours) and activity of the entrapped enzyme was confirmed by the pink color of the film that is indicative of the laccase-catalyzed oxidization of syringealdizine.

EXAMPLE 7

Encapsulation of Ubiquinone in a Cellulose Film Matrix

Ubiquinone (Coenzyme Q; Sigma Chemical Co.) is a membrane-bound electron carrier employed in the electron transport chain for production of cellular energy and the possibility of its encapsulation can lead to biologically conducting cellulose films regenerated from ionic liquids. Microcrystalline cellulose purchased from Sigma Chemical Co. (St. Louis, Mo.) was dissolved in [C$_4$mim]Cl using 3–5 second microwave pulses to create a viscous mixture. The mixture was cooled to room temperature from about 120–130° C., ubiquinone was added with stirring, and the resulting composition was cast into a film. The film was subsequently washed three times with water to rid the film of excess IL.

Figure 7:
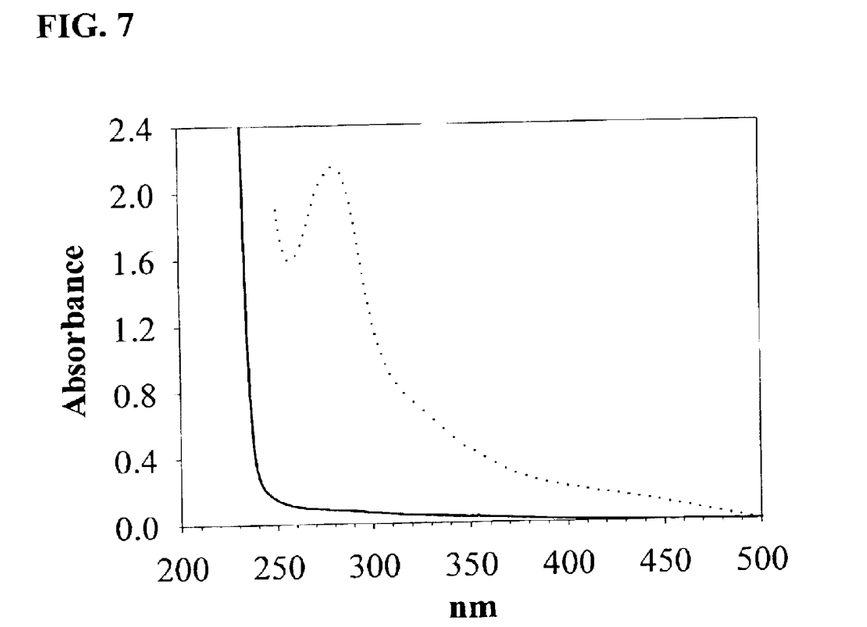
FIG. 7 is a UV/vis spectrum of a cellulose film alone (solid line) and cellulose film containing ubiquinone (dotted line).

The resulting film was permitted to dry for two days and then subjected to UV/vis Scan (500–250 nm) on a Varian Cary-3 spectrophotometer. A peak corresponding to the encapsulated Coenzyme Q was clearly visible at about 280 nm, which corresponds to aromatic moieties that exist in the biomolecule but not in native, IL-regenerated cellulose films. This spectrum is shown in FIG. 7.

EXAMPLE 8

Formation of Magnetic Cellulose Particles

Cellulose (1 g, Whatman filter paper substantially homogeneously) was dissolved in [C$_4$mim]Cl (20 g) by heating at 120 C. for 6 hours to form a 5 weight percent solution. Magnetite particles (1 g, about 5 micron powder; Aldrich Chemical Co.) were added to the molten solution and homogeneously distributed by vortexing the solution.

A lozenge of cellulose/magnetite composite was then-prepared by coating a plastic sheet (about 6×1.5 inch) with a film of the ionic liquid mixture. The sheet was placed in a bath containing deionized water and left to stand for 24 hours permitting all IL to be dissolved and diffuse from the matrix. The lozenge was then washed and maintained in distilled water. The resulting soft, flexible cellulose/magnetite film was air dried to yield a hard, brittle black solid.

Visual inspection using an optical microscope showed that the magnetite particles appeared to be disperse. The cellulose film was magnetic, and was attracted to a permanent magnet. Thermal gravimetric analysis of the air-dried film showed about 50 percent mass loss between 100–400° C., confirming that all the magnetite was entrapped within the regenerated composite retaining the initial composition ratio of 1:1 cellulose:magentite.

Each of the patents, applications and articles cited herein is incorporated by reference. The use of the article "a" or "an" is intended to include one or more.

From the foregoing it will be observed that numerous modifications and variations can be effectuated without departing from the true spirit and scope of the novel concepts of the invention. It is to be understood that no limitation with respect to the specific embodiment illustrated is intended or should be inferred. The disclosure is intended to cover by the appended claims all such modifications as fall within the scope of the claims.

What is claimed:

1. A method for forming a regenerated cellulose-encapsulated active substance that comprises the steps of:

(a) providing a composition of cellulose dissolved in a molten hydrophilic ionic liquid solvent along with an active substance dissolved or dispersed substantially homogeneously therein, said solution being substantially free of water, organic solvent or nitrogen-containing base, wherein said ionic liquid is comprised of cations and anions;

(b) admixing said solution with a liquid non-solvent for said cellulose that is miscible with said ionic liquid, said active substance being substantially insoluble in said non-solvent, said admixing forming a regenerated cellulose solid phase and an ionic liquid phase, whereby said active substance is encapsulated and substantially homogeneously dispersed in the formed regenerated cellulose solid phase, and wherein said regenerated cellulose has substantially the same molecular weight as the cellulose of step (a) and is substantially free of ionic liquid degradation products.

2. The method according to claim 1 wherein said ionic liquid is molten at a temperature of less than about 150° C.

3. The method according to claim 1 wherein the cations of said ionic liquid correspond in structure to a formula selected from the group consisting of wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate.

4. The method according to claim 1 wherein the anions of said ionic liquid are a halogen ion, perchlorate, a pseudohalogen ion or $C_1$–$C_6$ carboxylate.

5. The method according to claim 1 including the further step of collecting the formed cellulose phase.

6. A method for forming a regenerated cellulose-encapsulated active substance that comprises the steps of:

(a) providing a composition of cellulose dissolved in a molten hydrophilic ionic liquid solvent that is molten at a temperature of less than about 150° C. along with an active substance dissolved or dispersed substantially homogeneously therein, said solution being substantially free of water, organic solvent, or nitrogen-containing base, wherein said ionic liquid is comprised of cations and anions, wherein the cations correspond in structure to a formula selected from the group consisting of wherein $R^1$ and $R^2$ are independently a $C_1$–$C_6$ alkyl group or a $C_1$–$C_6$ alkoxyalkyl group, and $R^3$, $R^4$, $R^5$, $R^6$, $R^7$, $R^8$ and $R^9$ ($R^3$–$R^9$), when present, are independently a hydrido, a $C_1$–$C_6$ alkyl, a $C_1$–$C_6$ alkoxyalkyl group or a $C_1$–$C_6$ alkoxy group, and the anions of the ionic liquid are halogen, pseudohalogen, or $C_1$–$C_6$ carboxylate and the anions of said ionic liquid are halogen or pseudohalogen; and (b) admixing said solution with a liquid non-solvent for said cellulose that is miscible with said ionic liquid, said active substance being substantially insoluble in said non-solvent, said admixing forming a regenerated cellulose solid phase and an ionic liquid phase, whereby said active substance is encapsulated and substantially homogeneously dispersed in the formed regenerated cellulose solid phase, and wherein said regenerated cellulose has substantially the same molecular weight as the cellulose of step (a) and is substantially free of ionic liquid degradation products; and (c) collecting the formed regenerated cellulose solid phase.

7. The method according to claim 6 wherein said ionic liquid is molten at a temperature of about −44° to about 120° C.

8. The method according to claim 6 wherein said liquid non-solvent for said cellulose that is miscible with said ionic liquid is also miscible with water.

9. The method according to claim 8 wherein said liquid non-solvent for said cellulose that is miscible with said ionic liquid and is also miscible with water is water, an alcohol, or a ketone.

10. The method according to claim 9 wherein said liquid non-solvent is water.

11. The method according to claim 6 wherein the cations correspond in structure to a formula selected from the group consisting of wherein $R^1$ and $R^2$ are independently a $C_1$–$C_6$ alkyl group or a $C_1$–$C_6$ alkoxyalkyl group, and $R^3$, $R^4$, $R^5$ ($R^3$–$R^5$) are independently a hydrido, a $C_1$–$C_6$ alkyl group, a $C_1$–$C_6$ alkoxyalkyl group or a $C_1$–$C_6$ alkoxy group and the anions of the ionic liquid are a halogen or pseudohalogen.

12. The method according to claim 11 wherein said cation is a N,N-1,3-di-$C_1$-$C_6$ alkyl imidazolium ion that corresponds in structure to Formula A 13. The method according to claim 12 wherein one of said N,N-1,3-di-$C_1$-$C_6$ alkyl groups is methyl.

14. The method according to claim 13 wherein $R^1$ is $C_1$–$C_4$-alkyl.

15. The method according to claim 14 wherein said $R^3$–$R^5$ groups are each hydrido.

16. The method according to claim 15 wherein said cations correspond in structure to Formula B.

17. The method according to claim 11 wherein said anions are chloride ions.

18. The method according to claim 6 wherein said cellulose is initially present in said solution in an amount of about 10 to about 25 weight percent.

19. The method according to claim 6 wherein said admixing step is carried out by extruding said cellulose solution through a die and into said non-solvent.

20. The method according to claim 6 wherein said active substance is selected from the group consisting of a microbial cell, herbicide, insecticide, fungicide, bactericide, repellent for an animal or insect, a plant growth regulator, fertilizer, a flavor or odor composition, catalyst, enzyme, photoactive agent, indicator, dye, and a UV adsorbent.

21. The method according to claim 6 wherein said active substance is coated with a hydrophobic ionic liquid prior to being dissolved or dispersed in said hydrophilic ionic liquid, and wherein said hydrophobic ionic liquid is not miscible with said liquid non-solvent diluent.

22. The method according to claim 21 wherein said hydrophobic ionic liquid is not soluble in said liquid non-solvent diluent.

23. A regenerated cellulose-encapsulated active substance that comprises an active substance substantially homogeneously distributed within a matrix of regenerated cellulose, wherein said regenerated cellulose (i) has about the same molecular weight as the original cellulose from which it is prepared, (ii) is substantially free of an increased amount of substituent groups relative to the starting cellulose, and is (iii) substantially free of entrapped ionic liquid degradation products.

24. The regenerated cellulose-encapsulated active substance according to claim 23 wherein the weight ratio of cellulose to active substance is about 1000:1 to about 1:2.

25. The regenerated cellulose-encapsulated active substance according to claim 23 wherein said active substance is selected from the group consisting of a microbial cell, herbicide, insecticide, fungicide, bactericide, repellent for an animal or insect, a plant growth regulator, fertilizer, a flavor or odor composition, catalyst, enzyme, photoactive agent, indicator, dye, and a UV absorbent.

26. The regenerated cellulose-encapsulated active substance according to claim 23 wherein said active substance is coated with a hydrophobic ionic liquid within said matrix of regenerated cellulose.

27. A regenerated cellulose-encapsulated active substance that comprises a hydrophobic ionic liquid-coated active substance substantially homogeneously distributed within a matrix of regenerated cellulose, wherein said regenerated cellulose (i) has about the same molecular weight as the original cellulose from which it is prepared, (ii) is substantially free of an increased amount of substituent groups relative to the starting cellulose, and is (iii) substantially free of entrapped ionic liquid degradation products.

* * * * *